(12) United States Patent
Jönsson

(10) Patent No.: US 7,754,166 B2
(45) Date of Patent: Jul. 13, 2010

(54) DISINFECTION APPARATUS WITH CONNECTION DEVICE

(75) Inventor: Christer Jönsson, Växjö (SE)

(73) Assignee: Getinge Disinfection AB, Vaxjo (SE)

( * ) Notice: Subject to any disclaimer, the term of this patent is extended or adjusted under 35 U.S.C. 154(b) by 609 days.

(21) Appl. No.: 11/578,692

(22) PCT Filed: Apr. 26, 2005

(86) PCT No.: PCT/SE2005/000602

§ 371 (c)(1),
(2), (4) Date: Aug. 30, 2007

(87) PCT Pub. No.: WO2005/102397

PCT Pub. Date: Nov. 3, 2005

(65) Prior Publication Data

US 2007/0286780 A1    Dec. 13, 2007

(30) Foreign Application Priority Data

Apr. 27, 2004    (SE) .................................... 0401074

(51) Int. Cl.
*A61L 2/00* (2006.01)

(52) U.S. Cl. .................. 422/300; 141/352; 137/516.27

(58) Field of Classification Search .................. 422/292, 422/296, 297, 300, 302, 303; 137/511, 516.27, 137/528; 134/104.1; 141/348, 349, 351, 141/352

See application file for complete search history.

(56) References Cited

U.S. PATENT DOCUMENTS

| 4,552,728 A | 11/1985 | Taylor |
| 5,225,160 A | 7/1993 | Sanford et al. |
| 6,041,794 A | 3/2000 | Lin et al. |
| 6,354,312 B1 | 3/2002 | Lin et al. |
| 6,555,054 B1 | 4/2003 | Kral et al. |
| 6,558,620 B1 | 5/2003 | Sanford et al. |
| 2003/0190256 A1 | 10/2003 | Halstead et al. |
| 2005/0214159 A1* | 9/2005 | Schwei et al. .................. 422/28 |

FOREIGN PATENT DOCUMENTS

| FR | 2773325 | 7/1999 |
| JP | 5-62247 | 8/1993 |
| JP | 11-4876 | 1/1999 |
| JP | 2000-51329 | 2/2000 |

* cited by examiner

*Primary Examiner*—Walter D Griffin
*Assistant Examiner*—Timothy Cleveland
(74) *Attorney, Agent, or Firm*—Harness, Dickey & Pierce, P.L.C.

(57) ABSTRACT

A disinfection apparatus is disclosed for disinfecting fluid cleaning of health care objects and the like. The disinfection apparatus includes a fluid system for supplying fluid to a chamber, an at least partially movably arranged first connecting part with an active and an inactive position, which is adjusted to a mobile object holder, which object holder is to be placed in the chamber and has a second connecting part connectable to the first connecting part. The first connecting part is movable, under the action of the pressure in the fluid system, between a position disconnected from the holder and a position connected to the active position, i.e. to the second connecting part. A fluid connectable mobile object holder is also disclosed, which is adapted to be placed in a chamber of a disinfection apparatus as stated above.

11 Claims, 5 Drawing Sheets

DISINFECTION APPARATUS WITH CONNECTION DEVICE

FIELD OF THE INVENTION

The present invention relates to a disinfection apparatus for disinfecting fluid cleaning of health care objects and the like, which disinfection apparatus comprises a fluid system for supplying fluid to a chamber, an at least partially movably arranged first connecting part with an active and an inactive position, which is adapted to a mobile object holder, which object holder is to be placed in the chamber and has a second connecting part connectable to said first connecting part.

The invention also relates to a fluid-connectable mobile object holder which is adapted to be placed in a chamber of a disinfection apparatus as stated above.

BACKGROUND ART

Disinfection apparatus of the above type are well known. They are used for decontamination, disinfection and/or sterilization of goods, instruments and other objects that are used, for instance, in hospitals, laboratories and in the pharmaceutical industry. In these fields, disinfection is an important activity to prevent, for instance, the spread of infection and bacterial growth. By disinfection is meant rendering harmless, and the absence of, pathogenic forms of life, such as organisms, infectious substances etc. Sterilisation which can be considered a disinfecting measure requires, however, a higher degree of cleanness and concerns the absence of all forms of life whether they are pathogenic or not.

One type of disinfection apparatus is provided with what is referred to as walk-in chambers, which are large enough for an individual to enter and/or large enough for a trolley/cart or other equipment to be inserted. These trolleys are usually adapted to carry one or more of the above objects.

Disinfection apparatus of this type usually have a disinfection chamber into which a plurality of nozzles open for disinfection fluid to be supplied. Disinfection fluid usually comprises liquids of varying types but may also be different kinds of gases, such as vapour or other disinfectants.

To provide improved disinfection of the objects that are placed on a trolley, the trolley is frequently pro-vided with fluid nozzles for fluid to be supplied. The trolley has a connecting part, which is designed for fluid connection to a corresponding connecting part in the chamber. The fluid supply to the trolley is also normally an optional flow to the other nozzles of the disinfection apparatus in the chamber.

Existing connecting parts in the chamber of this type may cause troubles, for instance be an obstacle when an operator is to move a trolley or a similar object into and out of the chamber, especially when the connecting part is positioned at the floor of the chamber. In addition to problems associated with the connecting part possibly being a considerable obstacle, it can also be a time-consuming and complicated operation to connect and disconnect the fluid supply. The operator who usually performs connection and disconnection of the trolley must also ensure that connection and disconnection is performed properly.

It is also desirable to be able to use the disinfection apparatus for disinfecting purposes also without trolleys to which fluid is supplied and in addition to be able to reduce at least one of the above problems.

Finally it is advantageous to provide a robust, cost-effective, user-friendly and reliable high quality disinfection apparatus.

SUMMARY OF THE INVENTION

The object of the present invention is to provide a disinfection apparatus which enables improvements in relation to prior-art disinfection apparatus in one or more of the above-mentioned aspects.

The object is achieved by a disinfection apparatus of the type mentioned by way of introduction, which is further characterised in that said first connecting part is movable, under the action of the pressure in said fluid system, between a position disconnected from said holder and a position connected to said active position, i.e. to said second connecting part.

The object is also achieved with a fluid-connectable mobile object holder which is adapted to be placed in a chamber of a disinfection apparatus as stated above.

The present invention, as defined in claims 1 and 11, gives several advantages; for instance when the holder is placed in the chamber, the fluid connection may occur in an automatic manner by the fluid pressure in the fluid system. The invention can thus reduce the problems related to connection and disconnection of the fluid sup-ply to the holder when, for example, the movability of said first connecting part provides a possibility of a reduced risk of its being an obstacle. Moreover, the invention may result in a simplified connecting process and, associated therewith, a reduced time expenditure.

By fluid cleaning is in the first place meant different types of liquids, such as water and other liquid-like cleaning agents which can be used in washer disinfectors. In the second place, fluids in a wider perspective are intended, where disinfection can also take place by cleaning and/or disinfecting fluid, such as one or more of water, vapour or other disinfectants. Thus also the term sterilization can be comprised, for which apparatus such as autoclaves can be mentioned.

By health care objects and the like are in the first place meant goods, instruments and other objects which have to be disinfected in, for instance, hospitals, laboratories, the pharmaceutical industry or the like. In the second place, goods, instruments and other objects in the above-mentioned fields are intended, which have to be sterilized and/or decontaminated and cleaned in other manners. The following can be mentioned as examples of health care objects: vessels, instrument containers, hospital beds, trolleys, wheelchairs, animal cages, machine parts for health care applications and bulky objects.

It is preferred for said first connecting part to be arranged to take said disconnected position at a low fluid pressure, thus allowing free movability of the object holder. Thus, the object holder can easily be moved into and out of the chamber at a low fluid pressure.

By low fluid pressure is in the first place meant when the pressure is zero or alternatively close to zero, upstream of the first connecting part. In the second place, a lower pressure in relation to the normal operating pressure is intended and at a sufficiently low pressure for said first connecting part to leave said active position towards said disconnected position.

Said first connecting part is advantageously arranged to give a varying movement to extend into the chamber, said first connecting part extending minimally into the chamber in said disconnected position at a low fluid pressure.

This reduces the potential risk of said first connecting part being an obstacle in the intended use of the disinfection apparatus. By a varying movement is meant a movement which has at least two different positions, thus resulting in adjustability.

According to a preferred embodiment, said first connecting part is substantially axially movable under the action of the pressure in said fluid system. The opposite said second connecting part can together with said first connecting part thus establish the required seal by a relative motion in essentially one direction, viz. in the axial direction.

In addition to said active position, said first connecting part is preferably, in the absence of said second connecting part, movable under the action of the pressure in said fluid system to a fluid-arresting position, in which the fluid flow is arrested in said first connecting part. The fluid-arresting position thus corresponds to a safety position when, for example, someone has put the holder in the wrong place, forgot to throttle the flow to the first connecting part or the like. This safety position can give advantages since the operator can use the same programme whether the second connecting part is available or not. The cleaning programme can thus be designed so that the fluid flow is shut off in the fluid system up to the first connecting part just after the first connecting part has moved to the fluid-arresting position, in which case the first connecting part returns to the inactive position.

Said first connecting part may consist of relatively movable parts which are operatively connected to a valve assembly which, when moving, in the absence of said second connecting part, are connected so that the valve assembly is made to close. Moreover one of the parts included in the valve assembly can be a sealing element which is arranged in the fluid passage of said first connecting part.

Said first connecting part is suitably substantially sleeve-shaped to be able to provide the required movability and seal.

According to one embodiment, said first connecting part has a fixed part and a telescopic sleeve and, movable therewith, an annular valve seat, said sealing element being connected to said fixed part and said sealing element having a downwards directed conical sealing surface which cooperates with the valve seat. The telescopic sleeve provides a possibility of taking, under the action of the fluid pressure, at least three positions, in which case the fluid-arresting position is obtained by the seal between the sealing element and the conical sealing surface.

The first connecting part can be arranged with an arm which is pivotable in the chamber and movable under the action of the pressure in said fluid system. In some applications, it may, for instance for space reasons, be advantageous that the first connecting part is pivoted inwards to the second connecting part on the object holder. The movement by means of the pivotable arm can also be combined with an axial movement.

BRIEF DESCRIPTION OF THE DRAWINGS

The invention will now be described with reference to the accompanying drawings, which for the purpose of exemplification illustrate preferred embodiments of the invention.

FIG. 3b shows an active position of the corresponding sections of the disinfection apparatus in FIG. 3a.

FIG. 3c shows a fluid-arresting position of the corresponding sections of the disinfection apparatus in FIG. 3a.

FIG. 5b shows an active position of the corresponding cross-section of the disinfection apparatus according to FIG. 5a.

DESCRIPTION OF PREFERRED EMBODIMENTS

Figure 1:
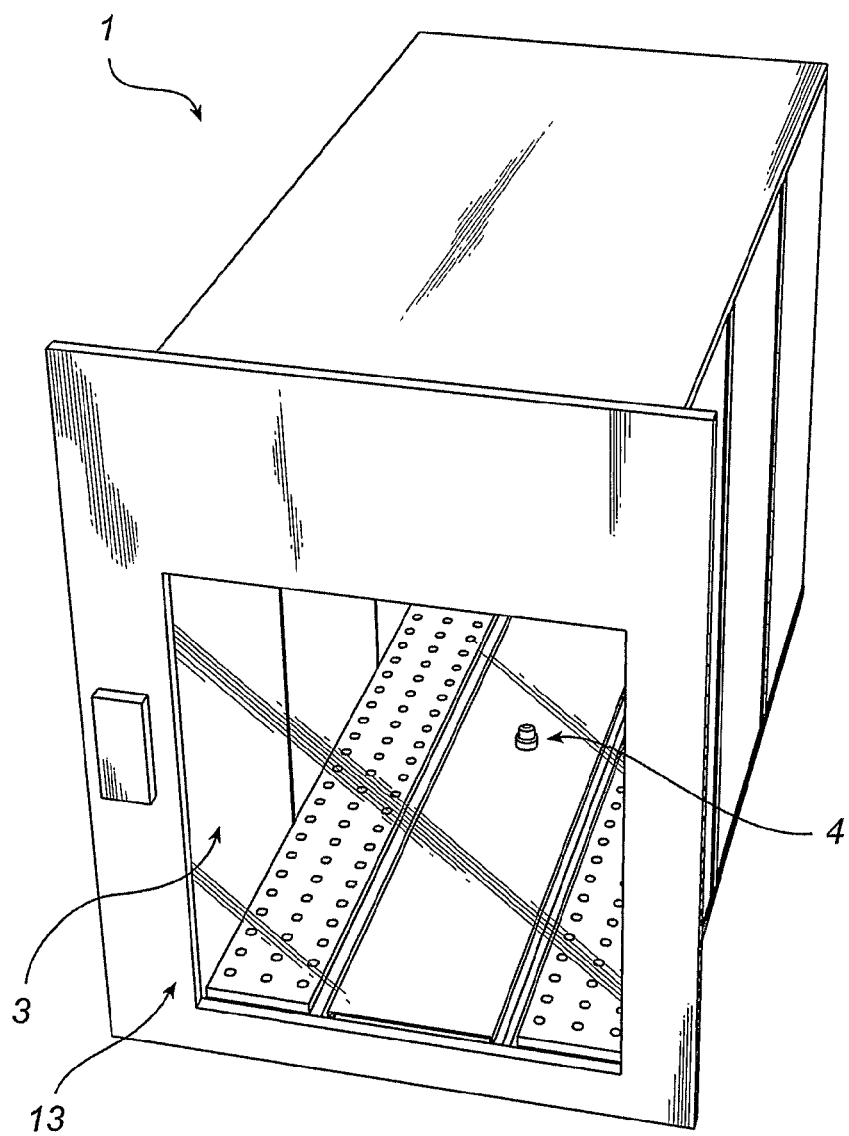
FIG. 1 is a schematic view of a disinfection apparatus according to a first embodiment of the invention.

FIG. 1 illustrates a disinfection apparatus 1 according to a first embodiment of the invention, which has a chamber 3 which is adapted to receive objects for disinfection. The chamber 3 is partly made from mountable wall, ceiling and floor elements of, for instance, stainless sheet steel. Moreover a movably arranged door 13 is mounted for opening and closing the entrance to the chamber.

Figure 2:
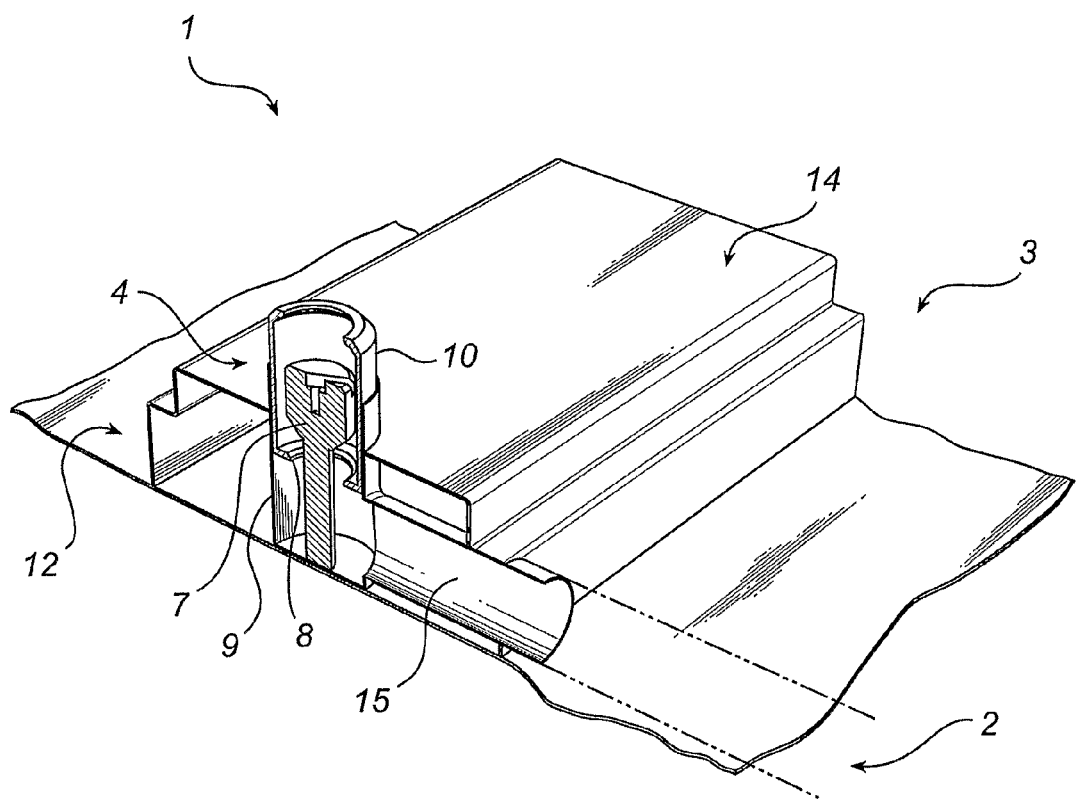
FIG. 2 shows in more detail parts of the disinfection apparatus in FIG. 1, partly in cross-section, seen obliquely from the front.

FIG. 2 shows a part of the bottom 12 of the chamber. A first connecting part 4 is arranged in a bent, substantially U-shaped metal sheet 14, with its opening oriented downwards. According to the first embodiment, the first connecting part 4 is arranged at the bottom 12 of the chamber, essentially in the centre of the extent of the bottom. The first connecting part 4 consists of a fixed part 9 in the form of an outer sleeve-shaped part of metal (or alternatively plastic) which is fixedly arranged in the bottom 12 of the chamber. A movably arranged sleeve 10 is positioned in the fixed sleeve-shaped part 9, their peripherally engaging surfaces being fluid-tight. The telescopic sleeve 10 has in its lower part a valve seat 8 in the form of a diametrical contraction. A sealing element 7 is, as shown in FIG. 2, centrally arranged in the lower part of the fixed sleeve part 9 at the bottom 12 of the chamber. In this case, the sealing element 7 is connected to the fixed sleeve part 9 by a screw joint. The free end of the sealing element 7 has an adjusted diameter in relation to the inner diameter 10 of the movable sleeve. As shown in FIG. 2, the sealing element 7 tapers downwards and thus has a downwardly directed conical sealing surface 11, which is complementarily sealable relative to the opposite valve seat 8 of the movable sleeve 10.

The fixed part 9 has a fluid line 15 arranged transversely to the longitudinal extent of the first connecting part, where the fluid line 15 extends along the bottom 12 of the chamber to a fluid system 2 for supplying fluid.

Figure 3A:
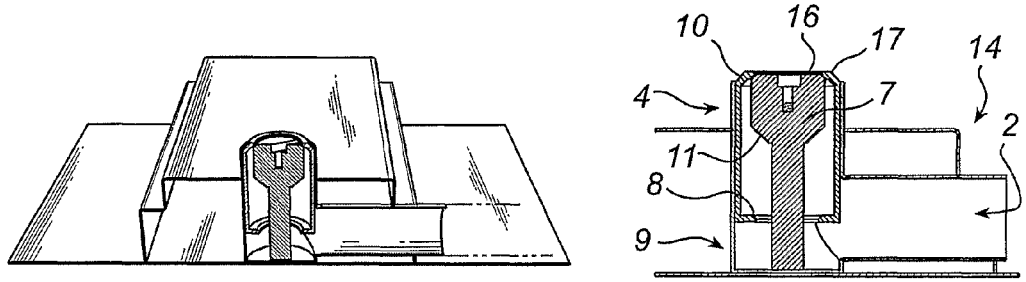
FIG. 3a shows two sections seen from the front of the disinfection apparatus in FIG. 2, in an inactive position.

The embodiment shown in FIG. 3a illustrates the first connecting part 4 in an inactive position when the movable sleeve 10 of the first connecting part 4 extends minimally into the chamber, thus reducing the risk of its being an obstacle to operators, trolleys and the like. In the inactive position, according to the first embodiment, the first connecting part 4 has substantially no fluid pressure relative to the pressure of the chamber. FIG. 3a shows that a free end 16 of the sealing element 7 is positioned at the same level as a connecting portion 17 at the level of the movable sleeve, which constitutes a sealing function, for example, for liquid descending into the chamber 3.

Figure 3B:
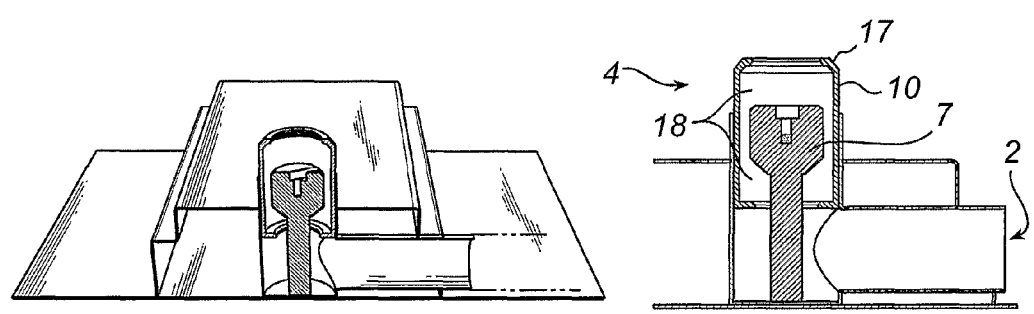
Figure 4:
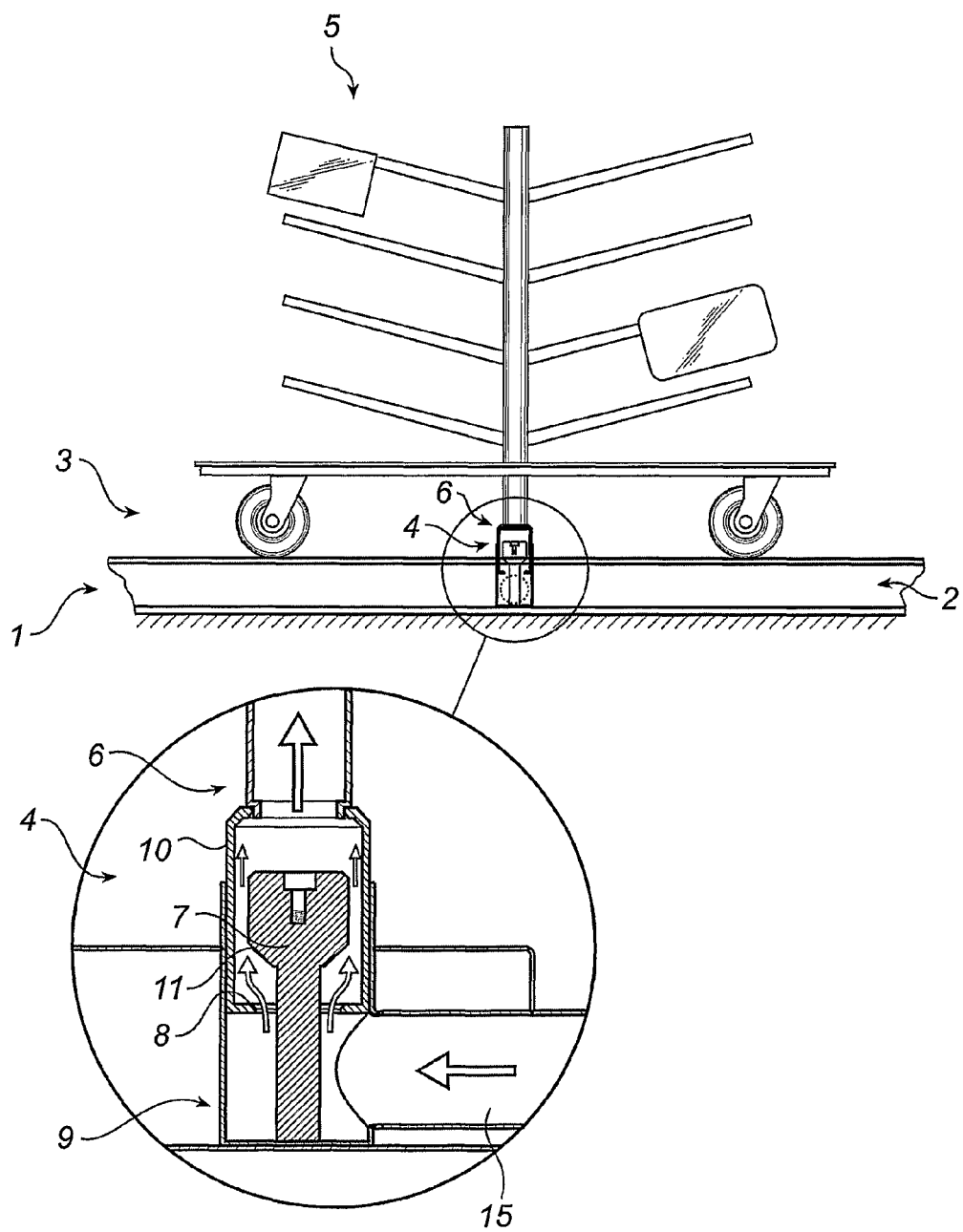
FIG. 4 shows the disinfection apparatus according to FIG. 1 with a fluid-connectable mobile object holder and a section of a first and a second connecting part.

FIG. 3b shows the first connecting part 4 in an active position, when the movable sleeve 10 of the first connecting part 4 has moved axially to form a peripheral fluid passage 18 around the sealing element 7 in the movable sleeve 10. FIG. 4 shows an object holder 5 in the form of a trolley which in its lower part has a second connecting part 6 which is adapted, in an active position, to be connected under the action of the pressure in the fluid line 15. This active position in FIG. 3b is also referred to as a connected position.

Figure 3C:
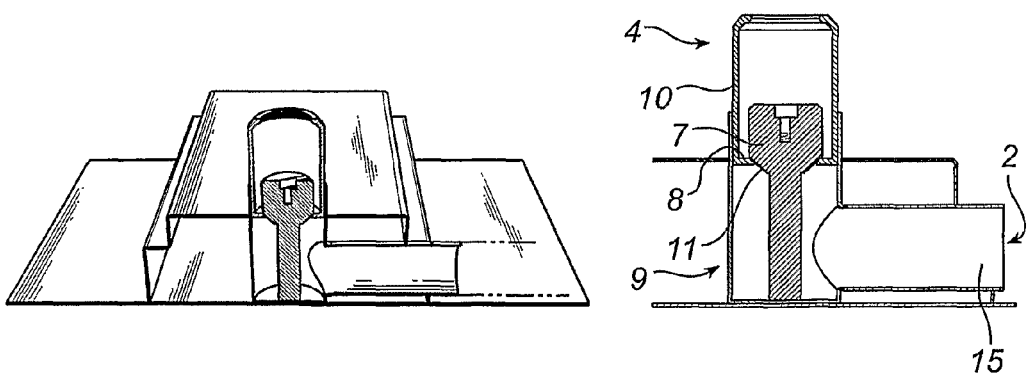

FIG. 3c illustrates the first connecting part 4 in a fluid-arresting position when the movable sleeve 10 of the first connecting part 4 has moved axially beyond the active position. This position can, for example, occur in the absence of said connecting part 6 on the object holder 5. In this fluid-arresting position, which is also referred to as a safety position, the annular valve seat 8 of the movable sleeve 10 moves under the action of the fluid pressure in the fluid line 15 into sealing abutment against the conical sealing surface 11.

With reference to FIGS. 4, 3a, 3b, 3c, the function of the disinfection apparatus according to the first embodiment will be described. The operator runs, for example, the trolley 5 carrying objects into the chamber 3 and closes the door 13. The operator starts the desired disinfection programme from a control unit (not shown). As fluid is supplied through the fluid line 15 in the fluid system 2, the fixed part 9 will be filled with fluid, whereby a pressure is applied to the lower part of the movable sleeve 10 adjacent to the valve seat. The flow area adjacent to the valve seat 8 is smaller than the corresponding area adjacent to the connecting portion 17. The movable sleeve 10 will thus, under the action of the pressure, move axially upwards. When the second connecting part 6 of the trolley is placed at a predetermined vertical distance above the first connecting part, it will thus be possible to arrange the connecting portion 17 to seal against the second connecting part 6, see FIG. 4. Fluid can then flow from the fixed part 9, through the fluid passage 18, into the second connecting part 6 and into the branches of the trolley and the associated nozzles (not shown) for distributing fluid in the chamber 3.

When the second connecting part 6 is not positioned above the first connecting part 4, in the intended way, the fluid pressure will thus affect the exterior of the lower part of the movable sleeve 10 adjacent to the valve seat 8, whereby the sleeve 10 is pressed axially upwards against the conical sealing surface 11 to the fluid-arresting position, see FIG. 3c. The sealing element 7 and the valve seat 8 cooperate under the action of pressure in this safety position for sealing abutment. According to the first embodiment, the disinfection programme is designed so that the fluid flow through the fluid line 15 is shut off by a pressure sensor and a control means (not shown) when the first connecting part 4 has moved to the fluid-arresting position. The pressure sensor can thus determine a pressure difference in the system and thus determine whether the first connecting part 4 has moved to the fluid-arresting position, in which case the control means according to the first embodiment deflects the liquid flow to an ordinary washing system with nozzles (not shown) in the chamber 3. Since this washing system is not part of the invention, it will not be described in more detail. The movable sleeve will then during the reduction of the fluid pressure return to the inactive position, see FIG. 3a. Consequently, the possible presence of the second connecting part 6 will be detected. This means that the same programme can be used whether the operator intends to use supply of fluid through the first connecting part, or not. In this case, the first connecting part 4 and its cooperating parts provide the functions of both automatic detection of the possible presence of the second connecting part 6 and automatic fluid connection. Moreover, the fluid-arresting position is advantageous in the absence of the second connecting part since there is no fluid flowing out of the first connecting part that may cause problems to objects in the chamber.

The disinfection apparatus 1 and the first and the second connecting part 4, 6 can according to a second embodiment be intended for the supply of gas, such as water vapour and other appropriate fluids. Since fluids (such as water and water vapour) at least to some extent have a similar behaviour, reference is made to the above description thereof. The first and the second connecting part 4, 6 will according to the second embodiment have a similar function even if the parts and fluid system 2 of the chamber will differ in certain respects as regards dimensioning and requirements as to tightness etc. Also the number of nozzles and their location on the holder (or the like) may differ with regard to the fact that gases have a better diffusion capacity than, for example, water in liquid form.

A third embodiment of the invention will be described in the following. Equivalent components have been given the same reference numerals, reference being made to the above description. The movably arranged sleeve 10 of the first connecting part 4 is according to the third embodiment arranged on an arm (not shown) which is pivot-able inwards relative to the chamber and which is movable under the action of pressure in the fluid line 15. A corresponding connecting portion 17 is arranged at the free end of the inwardly pivotable arm. The pivoting motion provides a possibility for the first connecting part 4 to be connected to the second connecting part 6 by the fluid pressure in a manner similar to that described above. The fluid-arresting position is provided according to the third embodiment by a valve-shaped design with a sealing element which is pivoted inwards and arrests the supply of fluid through a corresponding fixed part 9. The pivotable arm will in the absence of the second connecting part 6 continue to pivot outwards beyond the active position, thereby arresting the fluid.

In the following, a fourth embodiment of the invention will be described with reference to FIG. 5a. Equivalent components have been given the same reference numerals, reference being made to the above description.

Also in this embodiment, the first connecting part 4' is substantially sleeve-shaped, where relatively movable parts are operatively connected to a valve assembly 7', 8'. In this case, the valve assembly 7', 8' is pro-vided by the sealing element 7, for instance according to FIG. 4 with the downwardly directed sealing surface 11, instead being arranged with an upwardly directed sealing surface 11', and the sealing element 7' being movably arranged, preferably substantially axially. The valve seat 8' is fixedly arranged, preferably in the fixed part 9'. The valve seat 8' has an annular downwardly directed surface which is adjusted to the opposite movable sealing surface 11' of the sealing element 7'.

With reference once more to FIG. 5a, the peripherally projecting sealing surface 11' is arranged on the lower part of the movable sleeve 10'. As shown in FIG. 5a, the movable sleeve 10' has recesses 40' (in this case four recesses) to provide suitable passages for the fluid and connecting portions 41' between the sealing surface 11' and the upper part of the sleeve 10'. The sleeve 10' is preferably axially movably arranged on a fixedly arranged guide means 42' to provide the necessary movability in different operative positions. When the fluid pressure is low, zero or close to zero, the movable sleeve is retained or returned to the inactive/disconnected position, see FIG. 5a. In this case returning occurs partly by gravity. According to the fourth embodiment, also a drain valve (not shown) is preferably arranged in the bottom portion 44' of the first connecting part 4'. The drain valve or a similar means is opened at a low fluid pressure, and the remaining fluid can be drained off from the first connecting part 4', which also accelerates the return of the movable sleeve 10' to the inactive/disconnected position. Alternatively, returning may occur by a spring means, such as a coil spring, which can be arranged between the movable sealing surface 11' and the fixed part 9'.

Figure 5A:
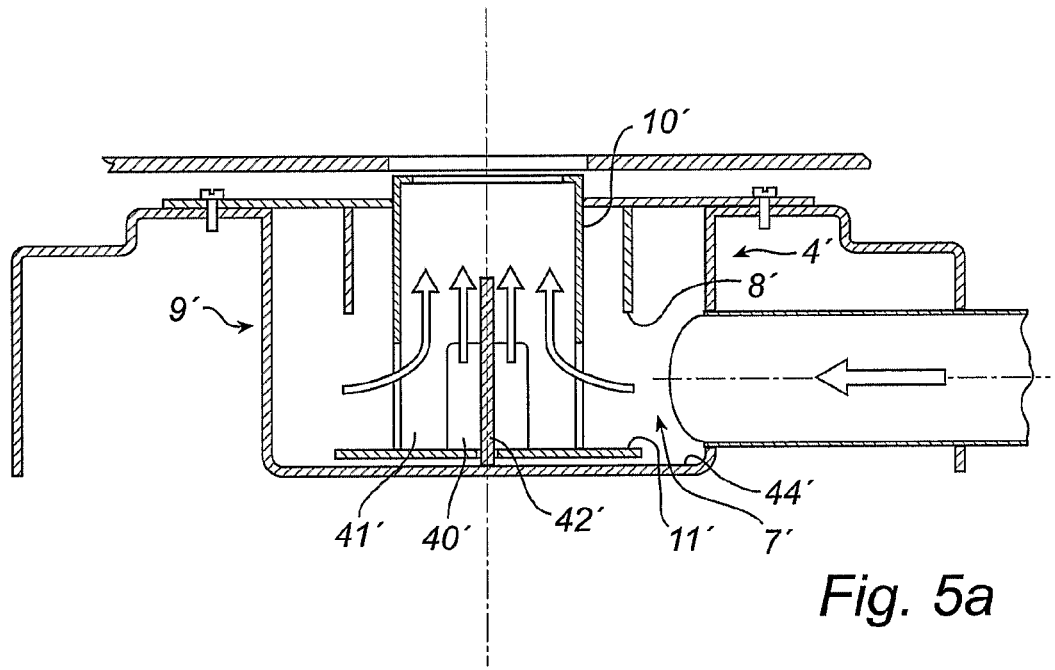
FIG. 5a is a schematic cross-section of parts of a disinfection apparatus with a first connecting part in an inactive position, according to a fourth embodiment of the invention.
Figure 5B:
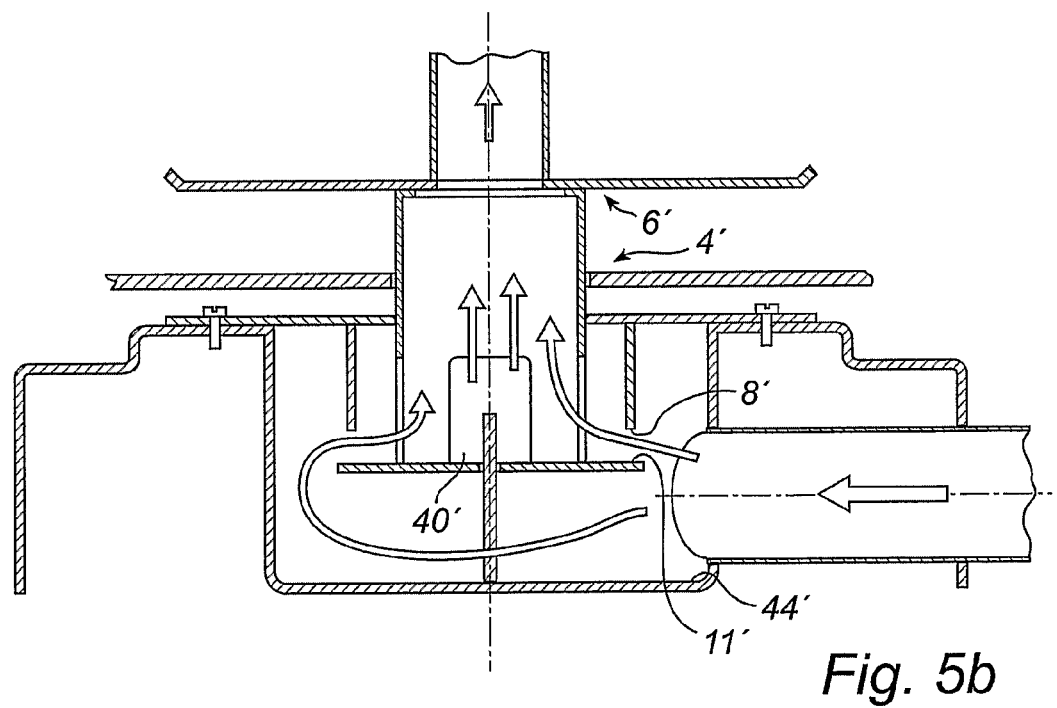

In the inactive position shown in FIG. 5a, the movable sleeve 10' extends minimally into the chamber so as not to be an obstacle to an operator, object holder etc. As the fluid pressure is increased, the fluid flows in through the recesses 40' and the fluid pressure affects the underside of the movable sleeve, thereby moving the sleeve upwards. If an object holder with a second connecting part is in the intended position, docking may thus occur, which is shown in FIG. 5b. The fluid can thus flow via the space between the sealing surface 11' and the valve seat 8' and then through the sleeve 10' to a second connecting part, if any. In the absence of a second connecting part 6' or the like, the sleeve 10' with the sealing surface 11' is moved on upwards under the action of the pressure to a fluid-arresting position. The fluid flow is arrested by the sealing surface 11' being pressed against the valve seat 8' so as thus to provide a valve-like function.

It will be appreciated that the above-described embodiments of the invention can be modified and varied by a person skilled in the art without departing from the inventive concept defined in the claims. The first connecting part 4 can, for example, be modified by said sealing element 7 with its downwardly directed sealing surface 11 instead being arranged with an upwardly directed sealing surface on the lower part of a movably arranged sealing element, the valve seat instead being fixedly arranged (for instance on said fixed part 9) so as to provide a valve-like function. Moreover connection can be performed, for example, by a combination of an axial and a pivoting movement.

Furthermore larger objects that are to be disinfected, such as large vessels, wheelchairs and hospital beds, can themselves be arranged with said second connecting part 6. Alternatively, the holder (wash trolley) can be provided with a fluid connection which in turn is connectable to the object.

Besides the disinfection apparatus may comprise a plurality of fluid connections, of which at least one is of the type defined as said first connecting part 4. For instance, there may be connections for supply of desalinated water (distilled water), for instance, to an after-rinsing step in the disinfection programme. Moreover a plurality of different liquids can be used in addition to water, dishwashing detergents, cleaning and disinfecting agents, which can have different pH values in the range 1.5-14.

The disinfection apparatus can also be adapted to use both liquids and gases each separately or in combination.

The invention claimed is:

1. A disinfection apparatus for disinfecting fluid cleaning of objects, the disinfection apparatus comprising:
a fluid system for supplying fluid to a chamber,
an at least partially movably arranged first connecting part with an active and an inactive position, adapted to a mobile object holder, the object holder being placeable in the chamber, and a second connecting part connectable to said first connecting part,
said first connecting part being movable, under the action of the pressure in said fluid system, between a position disconnected from said holder and a position connected to said second connecting part.

2. A disinfection apparatus as claimed in claim 1, wherein said first connecting part is arranged to take said disconnected position at a low fluid pressure, thus allowing free movability of the object holder.

3. A disinfection apparatus as claimed in claim 2, wherein said first connecting part is arranged to give a varying movement to extend into the chamber,
said first connecting part extending minimally into the chamber in said disconnected position at a low fluid pressure.

4. A disinfection apparatus as claimed in claim 1, wherein said first connecting part is substantially axially movable under the action of the pressure in said fluid system.

5. A disinfection apparatus as claimed in claim 1, wherein said first connecting part, in the absence of said second connecting part, is movable under the action of the pressure in said fluid system to a fluid-arresting position, in which the fluid flow is arrested in said first connecting part.

6. A disinfection apparatus as claimed in claim 5, wherein said first connecting part includes relatively movable parts which are operatively connected to a valve assembly which, when moving, in the absence of said second connecting part, are connected so that the valve assembly is made to close.

7. A disinfection apparatus as claimed in claim 6, wherein one of the parts included in the valve assembly is a sealing element, arranged in the fluid passage of said first connecting part.

8. A disinfection apparatus as claimed in claim 1, wherein said first connecting part is substantially sleeve-shaped.

9. A disinfection apparatus as claimed in claim 7, wherein said first connecting part includes a fixed part and a telescopic sleeve and, movable therewith, an annular valve seat,
said sealing element being connected to said fixed part and said sealing element including a downwards directed conical sealing surface which cooperates with the valve seat.

10. A disinfection apparatus as claimed in claim 1, wherein said first connecting part is arranged with an arm, pivotable in the chamber and movable under the action of the pressure in said fluid system.

11. A disinfection apparatus as claimed in claim 2, wherein said first connecting part is arranged with an arm, pivotable in the chamber and movable under the action of the pressure in said fluid system.

* * * * *